(12) United States Patent
Takai et al.

(10) Patent No.: US 7,282,620 B2
(45) Date of Patent: Oct. 16, 2007

(54) TYPE III ALLERGIC INFLAMMATION MODEL ANIMAL

(75) Inventors: Toshiyuki Takai, Sendai (JP); Masao Ono, Sendai (JP); Takae Yuasa, Osakasayama (JP); Takeshi Watanabe, Saga (JP)

(73) Assignee: Japan Science and Technology Agency, Kawaguchi-shi, Saitama (JP)

( * ) Notice: Subject to any disclaimer, the term of this patent is extended or adjusted under 35 U.S.C. 154(b) by 735 days.

(21) Appl. No.: 10/362,593

(22) PCT Filed: Aug. 23, 2001

(86) PCT No.: PCT/JP01/07196

§ 371 (c)(1),
(2), (4) Date: Feb. 24, 2003

(87) PCT Pub. No.: WO02/15680

PCT Pub. Date: Feb. 28, 2002

(65) Prior Publication Data

US 2003/0182667 A1  Sep. 25, 2003

(30) Foreign Application Priority Data

Aug. 24, 2000  (JP) .............................. 2000-253984

(51) Int. Cl.
*A01K 67/027* (2006.01)
*A01K 67/033* (2006.01)
*C12N 14/00* (2006.01)

(52) U.S. Cl. .............................. 800/18; 800/8; 800/14; 800/23

(58) Field of Classification Search ...................... None
See application file for complete search history.

(56) References Cited

U.S. PATENT DOCUMENTS 5,859,314 A  1/1999 Hibbs et al.

FOREIGN PATENT DOCUMENTS

WO  WO97/14791 A1  4/1997

OTHER PUBLICATIONS

Campbell and Wilmut, 1997, Totipotency or multipotency of cultured cells: applications and progress, Theriogenology, vol. 47, pp. 63-72.*
Mullins, 1996, J. Clin. Invest., vol. 97, pp. 1557-1560.*
Nishizumi, H et al. 1995, Impaired proliferation of peripheral B cells and indication of autoimmune disease in lyn-deficient mice, Immunity, 3:549-560.*
Takae, Y et al. Mar. 2001, Lyn is essential for Fcg Receptor III-mediated systemic anaphylaxis but not for the Arthus reaction, J Exp Med., 5:563-571.*
Hibbs, M.L. et al., "Multiple Defects in the Immune System of Lyn-Deficient Mice, Culminating in Autoimmune Disease", Cell, vol. 83, pp. 301-311, Oct. 20, 1995.
Oliver, J.M. et al., "Immunologically mediated signaling in basophils and mast cells: finding therapeutic targets for allergic diseases in the human Fc ε RI signaling pathway", Immunopharmacology, vol. 48, pp. 269-281, Jul. 25, 2000.
Takai, T. et al., "Regulation of murine hypersensitive responses by Fc receptors", Allergology International, vol. 47, No. 2, pp. 75-83, 1998.
Dombrowicz, D. et al., "Abolition of Anaphylaxis by Targeted Disruption of the High Affinity Immunoglobulin E Receptor @ Chain Gene", Cell, vol. 75, pp. 969-976, Dec. 3, 1993.
Takai, T. et al., "FcR γ Chain Deletion Results in Pleiotrophic Effector Cell Defects", Cell, vol. 76, pp. 519-529, Feb. 11, 1994.
Takai, T. et al., "Augmented humoral and anaphylactic responses in FcγRII-deficient mice", Nature, vol. 379, pp. 346-349, Jan. 1996.
Hiroshi Fujiwara et al., "The absence of IgE antibody-mediated augmentation of immune responses in CD23-deficient mice", Immunology, vol. 91, pp. 6835-6839, Jul. 1994.
Diana L. Sylvestre et al., "Fc Receptors Initiate the Arthus Reaction: Redefining the Inflammatory Cascade", Science, vol. 265, pp. 1095-1098, Aug. 19, 1994.
Takae Yuasa et al., "Deletion of Fcγ Receptor IIB Renders H-2 Mice Susceptible to Collagen-induced Arthritis", J. Exp. Med., vol. 189, No. 1, pp. 187-194, Jan. 4, 1999.
Sandra Kleinau et al., "Induction and Suppression of Collagen-induced Arthritis Is Dependent on Distinct Fcγ Receptors", J. Exp. Med., vol. 191, No. 9, pp. 1611-1616, May 1, 2000.
Yusuke Suzuki et al., "Distinct contribution of Fc receptors and angiotensin II-dependent pathways in anti-GBM glomerulonephritis", Kidney International, vol. 54, pp. 1166-1174, Jan. 26, 1998.

(Continued)

Primary Examiner—Valarie Bertoglio
(74) Attorney, Agent, or Firm—Venable, LLP; Robert Kinberg; Ann S. Hobbs (57) ABSTRACT

The present invention provides an experimental model animal which does not develop anaphylaxis, a type I allergy, can specifically induce Arthus reaction, a type III allergy, is not affected by type I allergy and evaluates type III allergy inflammation individually, and a method of screening a reaction accelerating or inhibitory substance in a type III allergy reaction through FcγRIII by using said experimental model animal. In order to eliminate FcγRIIB that demonstrates suppressive action to response through FrγRIII, a mouse wherein the deletion mutation of both molecules of Lyn and FcγRIIB are homozygotic (Lyn⁻IIB⁻) was generated by mating Lyn knockout mouse (Lyn⁻/⁻) and FcγRIIB knockout mouse (FcγRIIB⁻/⁻), and was used to measure and evaluate the deficiency of FcγRIII function in systemic passive anaphylaxis and the reduction of FcγRIII function in a bone marrow-derived mast cell, or the like.

1 Claim, 5 Drawing Sheets

OTHER PUBLICATIONS

Hisashi Wakayama et al., "Abolition of anti-glomerular basement membrane antibody-mediated glomerulonephritis in FcRγ-deficient mice", Eur. J. Immunol., vol. 30, pp. 1182-1190, 2000.

Raphael Clynes et al., "Uncoupling of Immune Complex Formation and Kidney Damage in Autoimmune Glomerulonephritis", Science, vol. 279, pp. 1052-1054, Feb. 13, 1998.

Akira Nakamura et al., "Fcγ Receptor IIB-deficient Mice Develop Goodpasture's Syndrome upon Immunization with Type IV Collagen: A Novel Murine Model for Autoimmune Glomerular Basement Membrane Disease", J. Exp. Med., vol. 191, No. 5, pp. 899-905, Mar. 6, 2000.

Jeffrey V. Ravetch et al., "Divergent Roles For Fc Receptors and Complement In Vivo", Annu. Rev. Immunol. vol. 16, pp. 421-432, 1998.

Marc Daëron, "Fc Receptor Biology", Annul. Rev. Immunol. vol. 15, pp. 203-234, 1997.

David Dombrowicz et al., "Absence of FcRI Chain Results in Upregulation of FcγRII-dependent Mast Cell Degranulation and Anaphylaxis", The J. Clin. Invest., vol. 99, No. 5, pp. 915-925, Mar. 1997.

Miyajima et al., "Systemic Anaphylaxis in the Mouse Can Be Mediated Largely through IgG1 and FcγRIII", The J. Clin. Invest., vol. 99, No. 5, pp. 901-914, Mar. 1997.

Azusa Ujike et al., "Modulation of Immunoglobulin (Ig) E-mediated Systemic Anaphylaxis by Low-Affinity Fc Receptor for IgG", J. Exp. Med., vol. 189, No. 10, pp. 1573-1579, May 17, 1999.

Elizabeth A. Finch et al., "Local calcium signalling by inositol-1,4,5-trisphosphate in Purkinje cell dendrites", Nature, vol. 396,24/31, pp. 753-756, Dec. 1998.

Carsten Schiller et al., "Mouse FcγRII is a negative regulator of FcγRIII in IgG immune complex-triggered inflammation but not in autoantibody-induced hemolysis", Eur. J. Immunol, vol. 30, pp. 481-490, 2000.

Margaret L. Hibbs et al., "*Lyn*, a *scr*-like Tyrosine Kinase", Int. J. Biochem Cell Biol., vol. 29, No. 3, pp. 397-400, 1997.

Tomohiro Kurosaki, "Genetic Analysis of B Cell Antigen Receptor Signaling", Annu. Rev. Immunol., vol. 17, pp. 555-592, 1999.

Hirofumi Nishizumi et al., "Impaired Tyrosine Phosphorylation and $Ca^{2+}$ Mobilization, but Not Degranulation, in Lyn-Deficient Bone Marrow-Derived Mast Cells", The J. of Immunology, pp. 2350-2355, 1997.

Y. Zhang et al., "Role of mast cells in plasma permeation due to immune injury of the skin basement membrane", Immunology, vol. 77, pp. 422-427, 1992.

Peter P. Bradley, et al., "Measurement of Cutaneous Inflammation: Estimation of Neutrophil Content with an Enzyme Marker", The J. of Invest. Dermatology, vol. 78, pp. 206-209, 1982.

Y. Okayama et al., "Multiple Cytokine mRNA Expression in Human Mast Cells Stimulated via FcεRI", Int. Arch Allergy Immunol, vol. 107, pp. 158-159, 1995.

Parris R. Burd et al., "Interleukin 3-Dependent and-Independent Mast Cells Stimulated with IgE and Antigen Express Multiple Cytokines", J. Exp. Med, vol. 170, pp. 245-257, Jul. 1989.

John R. Gordon et al., "Mast cells as a source of both preformed and immunologically inducible TNF-α/cachectin", Nature, vol. 346, pp. 274-276, Jul. 19, 1990.

Marshall Plaut et al., "Mast cell lines produce lymphokines in response to cross-linkage of FcεRI or to calcium ionophores", Nature, vol. 399, pp. 64-67, May 4, 1989.

Aribert Stief et al., "Mice Deficient in CD23 Reveal Its Modulatory Role in IgE Production but Not Role in T and B Cell Development", J. of Immunology, pp. 3378-3390, 1994.

Grzegorz Grynkiewicz et al., "A New Generation of $Ca^{2+}$ Indicators with Greatly Improved Fluorescence Properties", The J. of Biological Chem., vol. 260, No. 6, pp. 3440-3450, Mar. 25, 1985.

Yuasa et al., Lyn is Essential for Fcγ Receptor III-mediated Systemic Anaphylaxis but Not for the Arthus Reaction, J. Exp. Med., vol. 193, No. 5. Mar. 5, 2001 (pp. 563-571)—XP-002426009.

De Andres, Belen et al., A regulatory role for Fcγ Receptors (CD16 and CD32) in hematopoiesis—Immunology Letters 68, (1999), pp. 109-113—XP-002426010.

De Andres, Belen et al., A regulatory role for Fcγ Receptors (CD16 and CD32) in the development of Murine B Cells—Blood vol. 92, No. 8, Oct. 15, 1998, pp. 2823-2829—XP-002426011.

Wang et al., Altered Antigen Receptor Signaling and Impaired Fas-mediated Apoptosis of B Cells in Lyn-deficient Mice, J. xp. Med. vol. 184, Sep. 1996, pp. 831-838—XP-002426012.

Nishizumi et al., A double Edged Kinase Lyn: A Positive and Negative Regulator for antigen Receptor-mediated Signals, J. Exp. Med, vol. 187, No. 8, Apr. 20, 1998, 1343-1348—XP-002426013.

* cited by examiner

■ Lyn⁻IIB⁻   □ IIB⁻

FIG 5

TYPE III ALLERGIC INFLAMMATION MODEL ANIMAL

TECHNICAL FIELD

The present invention relates to an experimental model animal for type III allergy inflammation that does not develop anaphylaxis, a type I allergy, and can specifically induce Arthus reaction, a type III allergy, and to a method of screening a reaction accelerating or inhibitory substance in a type III allergy reaction through FcγRIII by using said experimental model animal.

BACKGROUND ART

It is known that immunoglobulin (Ig) is found in the body fluids of all vertebrate animals from fish to mammals, and is produced by lymphoid cells. It is classified into five classes, namely, IgG, IgM, IgA, IgD and IgE, according to the physicochemical and immunological properties, wherein the fundamental structure of molecules are common to each class, and is composed from H chain having fifty to seventy thousand molecular weight and L chain having twenty-three thousand molecular weight, and the H chain is structured with γ, μ, α, δ, and ε chain corresponding to IgG, IgM, IgA, IgD and IgE. The two H chains from the hinge region to the C terminal obtained by decomposing this Ig molecule with papain, which are bound by S—S binding is called a Fc fragment, and the receptor on the cell surface which this Fc fragment binds to is called a Fc receptor (hereinafter "FcR"). It is known that these FcRs derive signaling in the cells and crosslink by antigen-antibody complex which is a ligand, thereby constructing a hematopoietic cell surface molecule family that induces the response of many effectors. Further, it is known that FcR, which shows affinity to the Fc region of Ig and exists on the cell surface, is involved in immunoresponses such as antibody-dependent cytotoxic reaction and hypersensitive reaction.

The types of FcRs known are Fcγ receptor that binds specifically to the γ chain of IgG in the body fluid, Fcε receptor that binds specifically to the ε chain of IgE, FcαR that binds specifically to the α chain of IgA, and the like. It is known that the Fc receptors of these immunocompetent cells have a significant relationship with cell function, and that many of them exist in the large portion of lymphocyte, a part of the T cell lymphocyte, mononuclear cell, neutrophil, basophil, macrophage, mastocyte (mast cell), platelet or the like. Further, these receptors play a role in the function of lymphocyte that is antibody-dependent, however, its inherent function is poorly understood. Fcγ receptor (hereinafter "FcγR") is classified mainly into three types, type I (CD64 antigen), type II (CD 32 antigen) and type III (CD 16 antigen), based on the similarity of gene structure. It is known that FcγRI is a glycoprotein with a molecular weight of 72 kDa, which binds to the IgG monomer with high affinity, and expresses on the monocyte and macrophage. FcγRII differs from the other FcRs in that it has low affinity to the IgG monomer, binds to the polyvalent IgG that has become an immunocomplex, and is widely expressed in the hematopoietic stem cells including monocyte, macrophage, polymorphonuclear (PMN) leukocyte, mast cell, platelet, some of the T cell lymphocytes and B cell lymphocytes. Further, it is known that FcγRIII is a low-affinity FcγR, which expresses in natural killer cell, macrophage, PMN and mast cell. It is also known that three types of receptors having different gene arrangements, FcγRIIA, FcγRIIB and FcγRIIC, exist in FcγRII, and that each of its chromosome is positioned in 1q23.

Recently, knockout mice for these FcR molecular groups have been generated continuously (Cell 75, 969-976, 1993; Cell 76, 519-529, 1994; Nature 379, 346-349, 1996; Immunity 5, 181-188, 1996; Nature 369, 753-756, 1994; J. Immunol. 152, 3378-3390, 1994; Proc. Natl. Acad. Sci. USA 91, 6835-6839, 1994), and the understanding of the physiological function of some of the FcRs have progressed. Moreover, the present inventors have generated a knockout mouse of FcR γ chain isolated and identified as a homodimeric molecule that is associated with FcεRI, which is a high-affinity receptor of IgE (Cell, 76, 519-529, 1994). It is also known that this FcRγ chain knockout mouse is deficient in the expression and function of FcR, at least in the three types of FcγRI, FcγRIII and FcεRI.

The FcR that expresses in the immunocytic group mentioned above is a molecule that begins various immunoreaction and inflammatory response to antibody dependency. Since FcR expresses by duplicating in multiple cell species, the role of individual FcRs became clear only after several mice whose FcR expression is genetically deficient was generated. Presently, it has been revealed that the role of FcR is involved in the onset of diseases such as allergy (Cell 75, 969-976, 1993; Cell 76, 519-529, 1994), Arthus reaction (Science 265, 1095-1098, 1994; Immunity 5, 387-390), rheumatoid arthritis (J. Exp. Med. 189, 187-194, 1999; J. Exp. Med. 191, 1611-1616, 2000), immunologic glomerulonephritis (Kidney Int. 54, 1166-1174, 1998; Eur. J. Immunol. 30, 1182-1190, 2000), autoimmune vasculitis (Blood 94, 3855-3863, 1999), systemic lupus erythematosus (Science 279, 1052-1054, 1998) and Goodpasture's syndrome (Goodpasture's; J. Exp. Med. 191, 899-906, 2000), as well as biophylaxis. Moreover, the essential role of FcR in the various immune processes is progressively elucidated by the finding of the mutate mouse mentioned above (Annu. Rev. Immunol. 16, 421-432, 1998; Annu. Rev. Immunol. 15, 203-234, 1997; Takai, T., and J. V. Ravetch. 1998. Fc receptor genetics and the manipulation of genes in the study of FcR biology. In Immunoglobulin Receptors and their Physiological and Pathological Roles in Immunity. J. G. J. van de Winkel and P. Mark Hogarth, editors. Kluwer Academic Publishers, Netherland, 37-48).

It has also been reported that the FcγRIII on the mast cell plays a primary role at the start of the two types of distinct immunoresponses, that is, IgG-dependent anaphylaxis (J. Clin. Invest. 99, 915-925, 1997; J. Clin. Invest. 99, 901-914, 1997; J. Exp. Med. 189, 1573-1579, 1999) and passive Arthus reaction (Science 265, 1095-1098, 1994; Immunity 5, 387-390, J. Exp. Med. 184, 2385-2392, 1996; Immunity 5, 181-188, 1996; Eur. J. Immunol. 30, 481-490, 2000). These immunoresponsive models are distinguished from one another by the difference of the period of development of the disease and histology. In anaphylaxis, skin edema and systemic blood supply failure (shock) are developed immediately after antigen exposure. In contrast, Arthus reaction is found a few hours after antigen exposure, as a tissue damage accompanied by hemorrhage. Presently, the formation of pathology of models that indicate these characteristics, are explained as a result of time-limited discharge of inflammatory mediator, for example, the preexisting substances such as histamine and serotonin, and substances that are newly synthesized such as arachidonic acid metabolite and cytokine. However, the intracellular mechanism involved in the development of pathology of these models remains unclear.

Meanwhile, it is known that Lyn belongs to the Src family kinase, associates with a variety of immunoreceptors that have ITAM motif (an amino acid sequence that is recognized and bound by the SH2 region of the intracellular tyrosine kinase), and has a function to begin intracellular signaling (Int. J. Biochem. Cell. Biol. 29, 397-400, 1997; Annu. Rev. Immunol. 17, 555-592, 1999). In a recent research using a Lyn deficient mouse, it was revealed that Lyn plays an essential role in the individual body, for B cells and mast cells to function normally (Cell 83, 301-311, 1995; Immunity 3, 549-560, 1995; Immunity 7, 69-81, 1997). In fact, in a Lyn deficient mouse, marked damage is shown in the cutaneous anaphylaxis reaction which is induced by IgE and antigen, and Lyn plays an important role in the signaling through FcεRI (J. Immunol. 158, 2350-2355, 1997).

As mentioned above, Lyn tyrosine kinase, which belongs to the Src family, associates functionally with a variety of receptors such as FcR and the like, and plays a significant role in intracellular signaling. In contrast, in an inflammatory response such as autoimmune disease, allergy reaction or the like, wherein the immunocomplex is involved, the role of the FcγR of IgG expressed in mast cells and the like are drawing attention. For example, it was revealed by research using knockout mice that FcγRIII activates mast cells through the immunocomplex, and on the contrary, FcγRIIB inhibits mast cells. However, it was not possible to make an evaluation of type III allergy inflammation independently, since normally, the FcγRIIB shows inhibitory action. An object of the present invention is to provide an experimental model animal that does not develop anaphylaxis, a type I allergy, can specifically induce Arthus reaction, a type III allergy, and can independently evaluate the type III allergy inflammation without being affected by type I allergy, and a method of screening a reaction accelerating or inhibitory substance in a type III allergy reaction through FcγRIII using said experimental model animal.

The inventors of the present invention have conducted intensive study to attain the object mentioned above, and generated a double deficient mouse of Lyn and FcγRIIB in order to eliminate FcγRIIB which inhibits the response through FcγRIII. The significance of the role of Lyn in the downstream of FcγRIII signaling was studied by inducing systemic passive anaphylaxis with IgG-immunocomplex. From the fact that systemic passive anaphylaxis is Lyn-requisite and reverse passive Arthus reaction is not Lyn-requisite, the pathway connected to the allergy response through FcγRIII has two pathways, Lyn-dependent and Lyn-independent, and the inventors focused attention on the function of Lyn-independent pathway in type III allergy reaction. Thus, the present invention had been completed.

DISCLOSURE OF THE INVENTION

The present invention relates to a non-human model animal for type III allergy inflammation wherein the animal does not develop anaphylaxis, a type I allergy, and specifically induces Arthus reaction, a type III allergy (claim 1); the non-human model animal for type III allergy inflammation according to claim 1, wherein the genetic function of Lyn and FcγIIB are deficient on its chromosome (claim 2); the non-human model animal for type III allergy inflammation according to claim 1 or 2, wherein the non-human model animal is a rodent (claim 3); and the non-human model animal for type III allergy inflammation according to any of claims 1 to 3, wherein the rodent is a mouse (claim 4).

Further, the present invention relates to a method of screening a reaction accelerating or inhibitory substance in a type III allergy reaction through FcγRIII, wherein a subject material is administered to the non-human model animal for type III allergy inflammation according to any of claims 1 to 4, followed by determination and evaluation of FcγRIII function of the non-human animal (claim 5); the method of screening a reaction accelerating or inhibitory substance in a type III allergy reaction through FcγRIII according to claim 5, wherein the determination and evaluation of FcγRIII function of the non-human animal is a determination and evaluation of endorectal temperature after administration of antigen, with a systemic passive anaphylaxis response intensity as an index (claim 6); the method of screening a reaction accelerating or inhibitory substance in a type III allergy reaction through FcγRIII, wherein a bone marrow-derived mast cell induced from a bone marrow cell derived from the non-human model animal for type III allergy inflammation according to any of claims 1 to 4, is contacted with a subject material in vitro, followed by determination and evaluation of FcγRIII function of the bone marrow-derived mast cell (claim 7); the method of screening a reaction accelerating or inhibitory substance in a type III allergy reaction through FcγRIII according to claim 7, wherein the determination and evaluation of FcγRIII function of the bone marrow-derived mast cell is a determination and evaluation of degranulation ability of mast cell, cytoplasmic calcium dynamics of mast cell, or tyrosine phosphorylation of total protein of mast cell (claim 8); the method of screening a reaction accelerating or inhibitory substance in a type III allergy reaction through the FcγRIII according to any of claims 5 to 8, wherein the method uses the non-human model animal for type III allergy inflammation according to any of claims 1 to 4 and a non-human animal wherein the genetic function of FcγIIB is deficient on its chromosome (claim 9); and a remedy for diseases caused by type III allergy reaction, wherein an inhibitory substance obtained from the method of screening a reaction accelerating or inhibitory substance in a type III allergy reaction through the FcγRIII according to any of claims 5 to 9 is used as an active ingredient (claim 10).

BEST MODE OF CARRYING OUT THE INVENTION

As the non-human model animal for type III allergy inflammation of the present invention, there is no particular limitation as long as it is a non-human animal which does not develop anaphylaxis, a type I allergy, and specifically induces Arthus reaction, a type III allergy. A non-human animal wherein the genetic function of Lyn and FcγIIB are both deficient on its chromosome can be specifically exemplified. The non-human animal wherein the genetic function of Lyn and FcγIIB are both deficient on its chromosome refers to, for example, a non-human animal wherein a part or the whole of the endogenous gene of non-human animal that encodes Lyn and FcγIIB are inactivated by gene mutation such as disruption, deficiency, substitution and the like, and the function to express Lyn and FcγIIB in a wild-type is lost, or the like. Further, as the non-human animal in the present invention, rodents such as mice, rats, guinea pigs and the like can be specifically exemplified, but are not limited to these examples. The method of generating the non-human animal wherein the genetic function of Lyn and FcγIIB are both deficient on its chromosome will now be explained, by giving mice wherein the genetic function of Lyn and FcγIIB are both deficient on its chromosome as an example.

First, mice wherein the genetic function of Lyn is deficient on its chromosome, that is, Lyn knockout mice ($Lyn^{-/-}$), are generated. Lyn knockout mice can be generated by the method as previously described (Immunity 3, 549-560, 1995), or the like. Specifically, a gene fragment obtained from a mouse gene library by methods such as PCR or the like is used to screen a Lyn gene. With the recombinant DNA technique, a part or the whole of the Lyn gene that was screened is substituted with a marker gene such as neomycin-resistant gene or the like. A targeting vector is constructed by introducing genes such as diphtheria toxin A fragment (DT-A) gene, herpes simplex virus thymidine kinase (HSV-tk) gene or the like into the 5' end side. This targeting vector that was constructed is linearized, and introduced into ES cells by methods such as electroporation or the like. Homologous recombination is conducted, and among its homologous recombinants, ES cells that indicate resistance to antibiotics such as G418, ganciclovir (GANC) and the like are selected. It is preferable to confirm whether the selected ES cells are the aimed recombinants, by methods such as Southern blot or the like.

The recombinant ES cells mentioned above are microinjected into the blastocysts of mice, said blastocysts are returned to the tentative parent mice, and chimeric mice are generated. These chimeric mice are mated with wild-type mice to obtain heterozygous mice, and these heterozygous mice are mated to obtain Lyn knockout mice. As a method to confirm whether the genetic function of Lyn in said Lyn knockout mice is deficient on its chromosome, methods such as examination by Southern blot or the like after separating DNA from a portion of a mouse tail base obtained by the method mentioned above, examination by Northern blot or the like after isolating RNA from the bone marrow cell or the like of said mice, and examination of the Lyn expression of said mice by Western blot or the like, can be exemplified.

In the same manner as that of the Lyn knockout mice, mice wherein the genetic function of FcγRIIB is deficient on its chromosome, that is, FcγRIIB knockout mice are generated. The FcγRIIB knockout mice ($FcγRIIB^{-/-}$) can be generated by the method as previously described (Nature 379, 346-349, 1996), in the same manner as the method of generating the Lyn knockout mice mentioned above, or the like.

A double knockout mouse wherein the genetic function of Lyn and FcγIIB are both deficient on its chromosome, that is, a mouse wherein the deletion mutation of both molecules of Lyn and FcγRIIB are homozygotes ($Lyn^-IIB^-$), can be generated by mating the Lyn knockout mouse ($Lyn^{-/-}$) mentioned above and a mouse of FcγRIIB knockout mouse ($FcγRIIB^{-/-}$) lineage. Further, an example of the mouse wherein the genetic function of FcγIIB is deficient on its chromosome in the present invention is the FcγRIIB knockout mice ($FcγRIIB^{-/-}$) mentioned above, more preferably, a $Lyn^{+/-}FcγRIIB^{-/-}$ mice ($IIB^-$) that are littermates of double knockout mice ($Lyn^-IIB^-$).

As a method of screening a reaction accelerating or inhibitory substance in a type III allergy reaction through FcγRIII of the present invention, there is no particular limitation as long as it is a method of screening wherein a subject material is administered to the non-human model animal for type III allergy inflammation which does not develop anaphylaxis, a type I allergy, and specifically induces Arthus reaction, a type III allergy of the present invention, such as the double knockout mouse ($Lyn^-IIB^-$) mentioned above, followed by determination and evaluation of FcγRIII function in said non-human animal, or a method of screening wherein a bone marrow-derived mast cell induced from bone marrow cells derived from the non-human model animal for type III allergy inflammation which does not develop anaphylaxis, a type I allergy, and specifically induces Arthus reaction, a type III allergy of the present invention, such as the double knockout mouse ($Lyn^-IIB^-$) mentioned above, is contacted with a subject material in vitro, followed by determination and evaluation of FcγRIII function in said bone marrow-derived mast cell. When screening is conducted, it is preferable to make a comparative evaluation of the degree of FcγRIII function with a non-human animal wherein the genetic function of FcγIIB is deficient on its chromosome, such as the aforementioned FcγRIIB knockout mouse ($FcγRIIB^{-/-}$), preferably a $Lyn^{+/-}FcγRIIB^{-/-}$ mouse ($IIB^-$) which is a littermate of the double knockout mouse ($Lyn^-IIB^-$).

As a method of determination and evaluation of FcγRIII function in the non-human animal mentioned above, for example, when a subject material is administered in vivo, a method of determination and evaluation of endorectal temperature after administration of antigen with the systemic passive anaphylaxis response intensity as an index, or a method wherein a substance contained in the granule discharged from eosinophils, mast cells and the like in the tissues are determined and evaluated by ELISA, Western blot, and the like, can be exemplified. When a subject material is contacted with bone marrow-derived mast cells in vitro, a method wherein the degranulation ability of said mast cells, the cytoplasmic calcium dynamics of mast cells, the tyrosine phosphorylation of total protein of mast cells or the like are determined and evaluated, can be given as examples.

As a candidate substance of a reaction accelerating or inhibitory substance in a type III allergy reaction through FcγRIII, which can be obtained by the method of screening in the present invention, an agonist or antagonist of FcγRIII, a protein, peptide or the like that has action to the signaling pathway independent of Lyn, can be exemplified. Further, as a remedy for diseases caused by type III allergy in the present invention, there is no particular limitation as long as an inhibitory substance that can be obtained from the method of screening a reaction accelerating or inhibitory substance in a type III allergy reaction through the FcγRIII according to any one of those previously described is used as an active ingredient. With the administration of said remedy to mammals and the like in an appropriate method, diseases caused by type III allergy reaction, such as serum sickness, glomerulonephritis, lupus nephritis, hypersensitivity pneumonitis, and the like can be cured.

The present invention will now be explained more specifically with the following examples, however, the technical scope of the invention is not limited to these examples.

EXAMPLE A

Material and Method

A-1 (Mice)

Seven to 12-week old mice kept in a condition where they are not infected with specific pathogens were used for all the experiments. Mice wherein the deletion mutation of both molecules of Lyn and FcγRIIB are homozygotic (Lyn$^-$IIB$^-$) were generated by mating Lyn$^{-/-}$ (Immunity 3, 549-560, 1995) and FcγRIIB$^{-/-}$ (Nature 379, 346-349, 1996) lineage mice. Further, the littermates, Lyn$^{+/-}$FcγRIIB$^{-/-}$mice (IIB$^-$) were used as controls of Lyn$^{-/-}$FcγRIIB$^{-/-}$mice (Lyn$^-$IIB$^-$) mentioned above.

A-2 (Cells and Antibodies)

Bone marrow-derived mast cells (BMMCs) were induced by culturing bone marrow cells with RPMI1640 [including 5 ng/ml mouse IL-3 (R&D Systems Inc, Minneapolis, Minn.), 10% immobilized fetal bovine serum, non-essential amino acid solution (GIBCO-BRL, Grand Island, N.Y.), 100 IU/ml penicillin, 100 μg/ml streptomycin and 10 μM 2-mercaptoethanol at a final concentration]. As to mouse-anti trinitrophenyl hapten (TNP) IgE (IGELa2; American Type Culture Collection) and mouse-anti-TNP IgG1 (G1; Cell. Immunol. 145, 299-310, 1992), each of their hybridoma culture supernatants were purified by DEAE-cellulose column chromatography. As to the rat anti-mouse FcγRII/III (2.4G2, PharMigen, San Diego, Calif.), rabbit IgG anti-ovalbumin (OVA; Sigma, St Louis, Mo.), F(ab')$_2$ fragment of goat anti-rat IgG (Immunotech, Cedex, France) and anti-phosphorylation tyrosine antibody (4G10; upstate Biotechnology, Lake Placid, N.Y.), those purchased were used.

A-3 (Induction of Systemic Passive Anaphylaxis)

Each of the mice generated in A-1 [Lyn$^{-/-}$FcγRIIB$^{-/-}$ (Lyn$^-$IIB$^-$) and Lyn$^{+/-}$FcγRIIB$^{-/-}$(IIB$^-$)] were sensitized with 20 μg of anti-TNP IgG or 20 μg of anti-TNP IgE by intravenous injection. Thirty minutes (IgG sensitization) or 24 hours (IgE sensitization) after the sensitization, 1 mg of TNP-linked OVA was dissolved in 100 ml PBS and this solution was intravenously injected to the mice to induce systemic passive anaphylaxis. Systemic passive anaphylaxis was induced to the controls by using the same amount of OVA instead of TNP-OVA during the induction. After the induction, a digital temperature indicator (Natume Seisakusyo Co., Osaka, Japan) with a temperature sensor probe was used to measure the endorectal temperature sequentially.

A-4 (Degranulation and Cytokine Release)

BMMCs (5×10$^4$ cell) were labeled with 6.6 μCi/ml of 5-[1,2-$^3$H]-hydroxytryptamine creatinine sulfate (Amersham Pharmacia Biotech) for 16 hours, 5 μg/ml of 2.4 G2 or 1 μg/ml of mouse anti-TNP IgE was added at the remaining 30 minutes, and their BMMCs were sensitized. After the antibodies that did not bind to BMMCs were eliminated, 0.3 to 10 μg/ml of goat anti-rat IgG F(ab')$_2$ fragment or 0.03 to 30 ng/ml of TNP-OVA was added and stimulated for one hour. The serotonin release rate (% of degranulation) was calculated in the same manner as reported previously (Cell 76, 519-529, 1994). The unlabeled BMMCs were stimulated in the same manner as mentioned above for cytokine release. After the stimulation, culture supernatant after 12 or 6 hours was used to measure the release of IL-4 or TNF-α, respectively. The amount of cytokine release was measured by using ELISA (Endogen, Inc., Woburn, Mass.).

A-5 (Cytoplasmic Calcium Dynamics)

BMMCs labeled with 2 μM of Fura-2/acetoxymethyl ester (Molecular Probes, Eugene, Oreg.) was sensitized under a condition of 25.degree. C. for ten minutes, with the use of 2 μg/ml of biotin-binding mouse-anti TNP IgE or 5 μg/ml of biotin-binding 2.4 G2. After eliminating the antibodies that did not bind, the sensitized cells mentioned above were stimulated with 10 μg of streptavidin (Wako Pure Chemicals, Osaka, Japan) in 2 ml of PBS containing 1 mM of CaCl$_2$ and 1 mM of MgCl$_2$. As to the cytoplasmic calcium dynamics, the excitation of 340 and 360 nm was measured by using a fluorescence spectrophotometer (Hitachi model F4500, Hitachi Ltd., Tokyo, Japan), at an emission wavelength of 510 nm. The measurement and conversion of calcium concentration was conducted according to the method described in the literature (J. Biol. Chem. 260, 3440-3450).

A-6 (Immunoblotting Analysis)

BMMCs (1×10$^6$) sensitized with 2.4G2 or biotin-binding mouse IgE were suspended in 100 μl of PBS containing 1 mM of CaCl$_2$ and 1 mM of MgCl$_2$. Each of the suspensions were added with 30 μg/ml of goat anti-rat IgG F(ab')$_2$ fragment or 5 μg/ml of streptavidin, and treated under a condition of 37.degree. C. for 0.5, 1 or 5 minutes. Adding the same amount of ice-cold solubilized solution (50 mM of Tris-HCl (pH 7.4), 1% of Nonident P-40, 137 mM of NaCl, 2 mM of EDTA, 50 mM of NaF, 2 mM of NaVO$_4$, 1 mM of phenylmethylsulfonyl, 10 mg/ml of aprotinin, 5 mg/ml of leupeptine and 2 mg/ml of pepstatin) completed these treatments. The cytolytic solution wherein the nucleus fraction had been eliminated was used for examination of phosphorylation of proteins. Anti-phosphorylation tyrosine antibody (4G10) was used to conduct immunoblotting.

A-7 (Reverse Cutaneous Passive Arthus Reaction)

Dorsal intracutaneous administration of physiological saline containing 0, 16 or 80 μg of rabbit anti-OVA IgG was performed to each of the mice obtained from Example A-1, whose trunk had been shaved. Immediately after, 200 μl of physiological saline containing 1 mg of OVA was intravenously injected to the mice. These mice were killed after eight hours, and the dorsal skin was collected. The method according to Bradley et al. (J. Invest. Dermatol. 78, 206-209, 1982)was used as a reference for the Myeloperoxidase (MPO) assay. Simply, the portions that developed inflammation were excised as small pieces of tissues (12.5 mm$^2$), homogenized with 400 μl of 50 mM phosphate solution (pH 6.0), further added with hexadecyltrimethylammonium bromide (HTAB; Sigma) to a concentration of 0.5%, crushed by sonication for 20 seconds, and freeze thawing was repeated three times to generate extracts. These extracts were centrifuged for 15 minutes at 14,000 rpm, and the supernatant obtained was used for measuring the MPO activity. 20 μl of these supernatant and 200 μl of substrate solution [50 mM of phosphate solution (pH 6.0), 0.167 mg/ml of o-dianisidine duhydrochloride (Sigma) and 0.0005% of hydrogen peroxide (Wako Pure Chemical)] were mixed, and the change of color of the substrate solution was measured at an absorbance of 460 nm. The MPO activity obtained from 0.25 μl of total mouse blood was calculated as 1 unit. For histological examination, the pieces of skin were fixed with 10% (vol/vol) neutral buffer formalin solution, made to paraffin pieces, followed by hematoxylin eosin staining.

EXAMPLE B

Results

B-1 (Deficiency of FcγRIII Function in Systemic Passive Anaphylaxis of Lyn$^{-/-}$FcγRIIB$^{-/-}$Mice)

It has been clarified from the previous studies that Lyn-deficient mice cannot develop cutaneous passive anaphylaxis caused by IgE. This fact indicates that Lyn plays an important role in the downstream of the signaling of FcεRI on the mast cell (Cell 83, 301-311, 1995). The present inventors used the Lyn and FcγRIIB double deficient mice (Lyn$^{-/-}$FcγRIIB$^{-/-}$mice: Lyn$^-$IIB$^-$) lineage described in Example A-1, in order to eliminate the FcγRIIB (Annu. Rev. Immunol. 15, 203-234, 1997; J. Exp. Med. 189, 1573-1579, 1999; Nature 379, 346-349, 1996), which acts in a suppressive way against the response through FcγRIII. This was done in order to examine the significance of the role of Lyn in the downstream of the signaling of FcγRIII, when systemic passive anaphylaxis is induced with IgG-immunocomplex.

Figure 1:
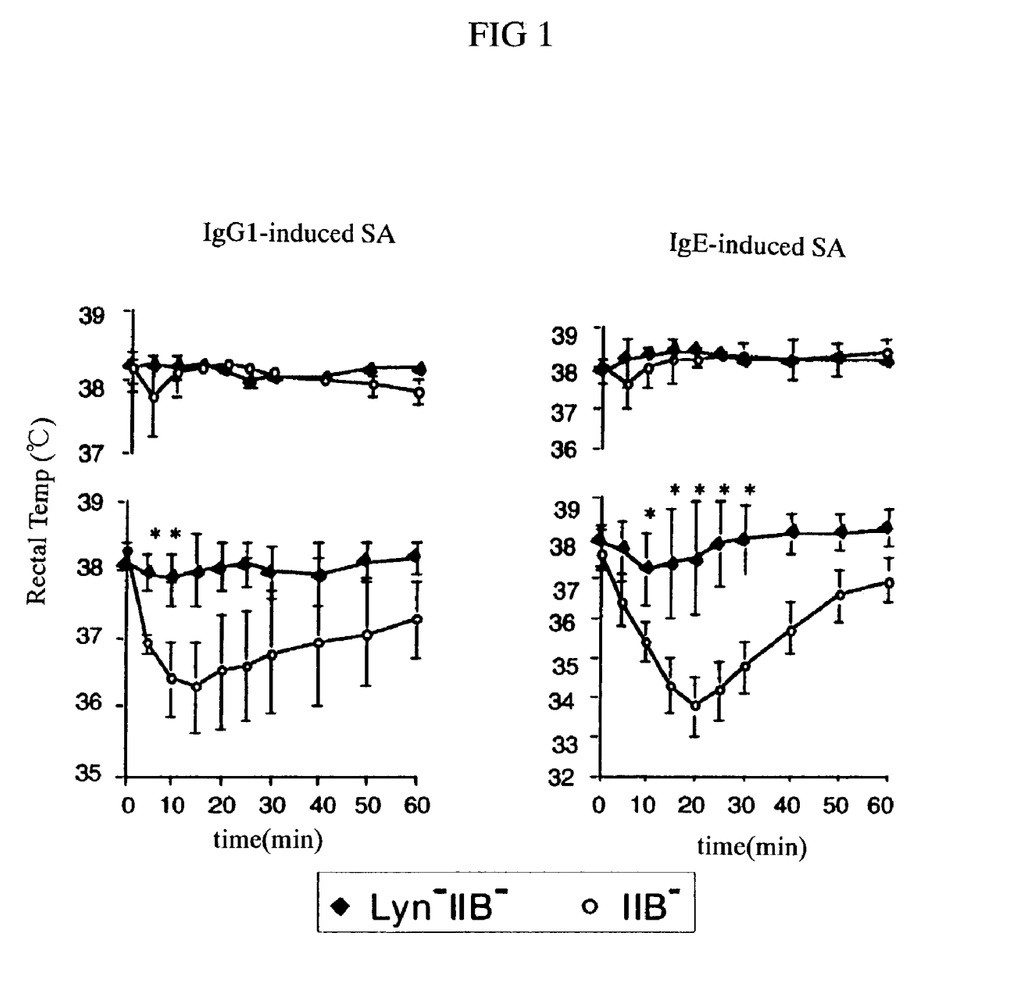
FIG. 1 is a view showing the results from monitoring the systemic passive anaphylaxis in the double deficient mice (Lyn⁻IIB⁻) of the present invention and control mice (IIB⁻), by endorectal temperature determination.

Following the method described in Example A-3, systemic passive anaphylaxis was induced to the double deficient mouse and control mouse, by administration of hapten-specific antibody [anti-TNP IgG1 (FIG. 1 left; n=4) or anti-TNP IgE (FIG. 1 right; n=6)] and antigen (TNP-OVA) through the coccygeal vein. The decrease in endorectal temperature from the time the antigen was administered was measured sequentially with the response intensity of the systemic passive anaphylaxis as an index. The results are shown in FIG. 1. It was confirmed that in the stimulation of IgG and IgE, the control mouse showed obvious response, whereas the double deficient mouse clearly showed reduced response. It was revealed that since the response is reduced in double deficient mouse, the Lyn activity in mast cell is necessary for anaphylaxis through FcγRIII as well as in anaphylaxis through FcεRI. As to control experiment (FIG. 1 upper case), endorectal temperature was measured in the same manner as the method described above, except that antibody was not administered to each of the mice mentioned above.

B-2 (Reduction of FcγRIII Function in the BMMCs Induced from Lyn Deficient Mice)

Figure 2:
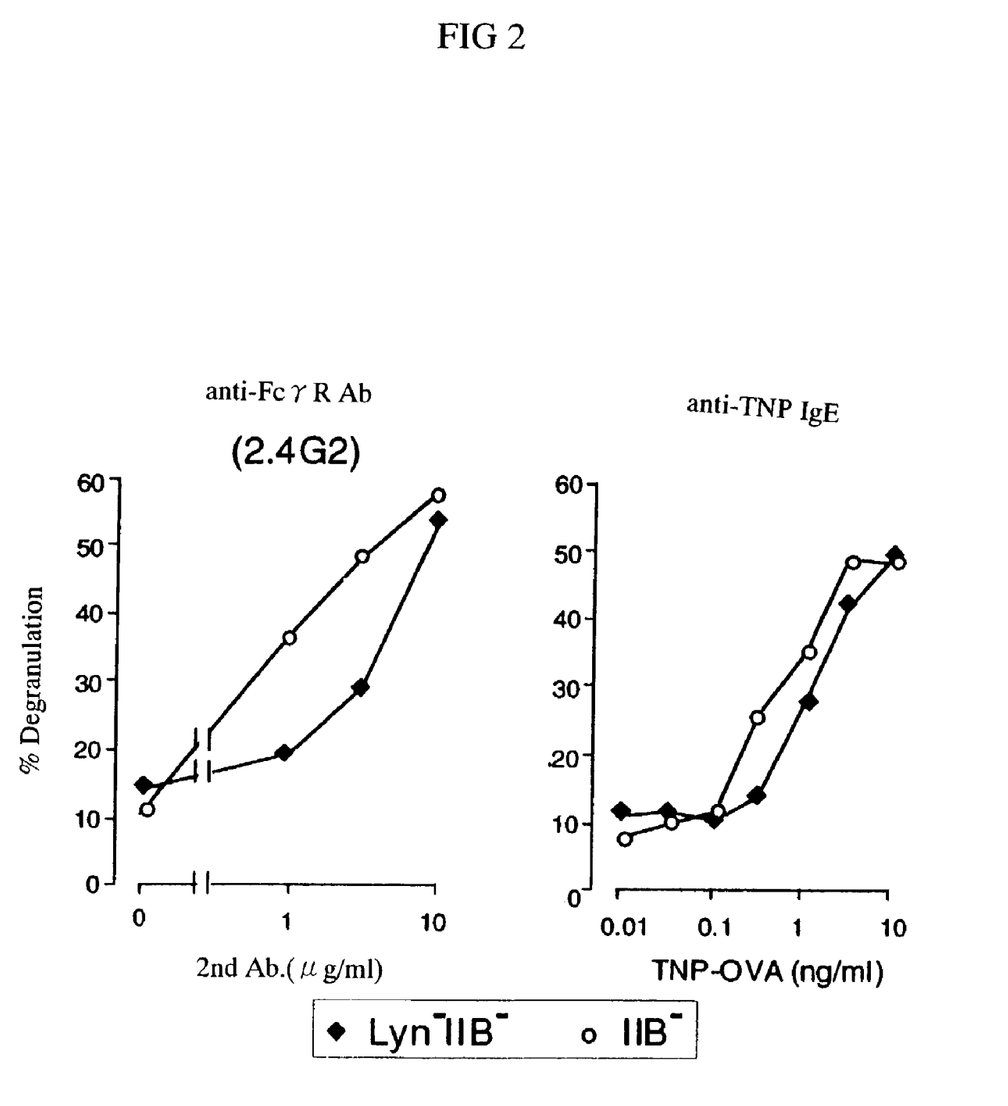
FIG. 2 is a view showing the results from monitoring the degranulation ability of bone marrow-derived mast cell of the double deficient mice (Lyn⁻IIB⁻) of the present invention and control mice (IIB⁻), by serotonin quantitative determination.

Next, in order to examine the degranulation ability of mast cells as an immediate response, and also as a main factor that develops anaphylaxis, functional analysis was conducted by examining the serotonin release using the culture BMMCs. FcγRIII or FcεRI was gradually crosslinked to induce the activity of mast cell, and the radiation-labeled serotonin released in the culture supernatant was measured (FIG. 2). Degranulation of BMMCs were induced by crosslinking FcγRIII and FcεRI with 2.42G2 and goat anti-rat IgG1 F(ab')$_2$ (FIG. 2 left) or anti-TNP IgE and TNP-OVA (FIG. 2 right). As to degranulation, serotonin released in the culture supernatant one hour after stimulation was determined according to the method described in Example A-4. It was revealed from these results that the double deficient mouse-derived BMMCs show low response to weak stimulation (1 to 3 μg/ml of anti-rat IgG and 0.3 to 3 ng/ml of TNP-OVA) by stimulation through FcγRIII and FcεRI. On the other hand, it was also found out that the same level of degranulation was shown for high stimulation in double deficient mouse-derived BMMCs. The differences between the double deficient mouse and control mouse were confirmed by an experiment repeated three times, and a cultured mast cell induced independently from the two mice were used for confirmation.

Figure 3:
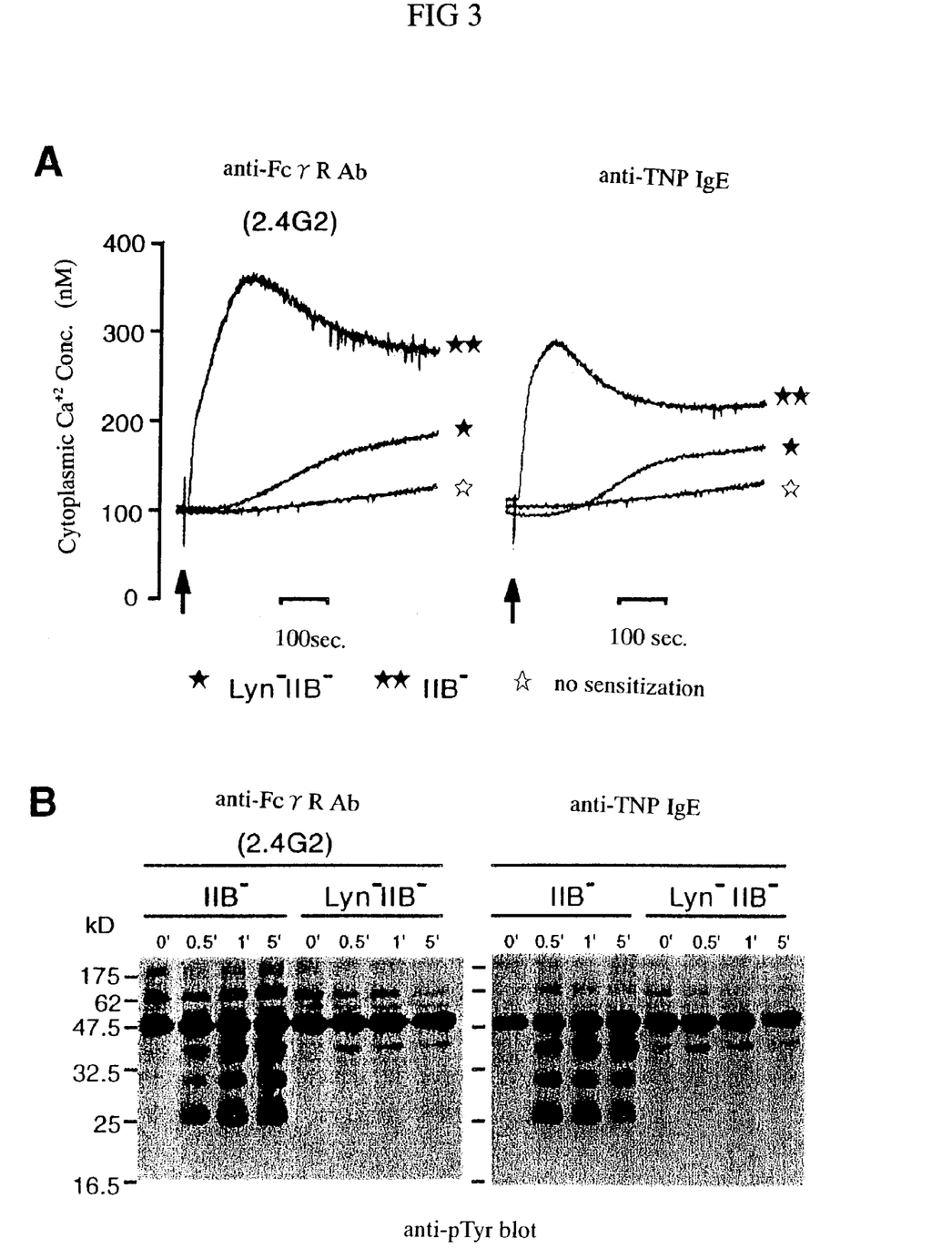
FIG. 3 is a view showing the results from determination of intracellular $Ca^{2+}$ dynamics of bone marrow-derived mast cell (A) and tyrosine phosphorylation of cell total proteins (B) of the double deficient mice (Lyn⁻IIB⁻) of the present invention and control mice (IIB⁻) which are induced by cross linkage of FcR.

The present inventors then examined the cytoplasmic calcium dynamics and the total protein tyrosine phosphorylation of cells as characteristics of the deficiency of intracellular function of double deficient mouse-derived BMMCs. The BMMCs were stimulated in the method as described in Example A-5, and the cytoplasmic calcium dynamics was measured with a fluorescence spectrophotometer in an excitation at 510 nm. The results are shown in FIG. 3A. The results showed that in double deficient mouse-derived BMMCs, the calcium dynamics by stimulation through FcγRIII or FcεRI reduced. This response was affected especially at an early stage (<150 seconds) after induction, and was sufficiently induced in a later stage (>300 seconds). The arrow in the Figure shows the cross linkage by streptavidin.

Further, BMMCs were stimulated in the method as described in Example A-5, the reaction was completed in the same manner as described in Example A-6, and immunoblotting was conducted to the cytolytic solution wherein the nucleus fraction had been eliminated (equivalent to 2.5×10$^4$ per 1 lane) by using an anti-phosphorylation tyrosine monoclonal antibody (anti-pTyr: 4G10). The results are shown in FIG. 3B. As is also clear from the results, it was revealed that five minutes after the stimulation, there was an effect in the induction of tyrosine phosphorylation in double deficient mouse-derived BMMCs. In addition, the expression of FcγRIII, FcεRI and c-kit, the proliferation by IL-3 and the uptake of serotonin was normal in double deficient mouse-derived BMMCs. This fact indicates that in double deficient mouse-derived BMMCs, functional abnormality (deficiency) was generated, not the differentiation abnormality such as small amount of expression of FcRs. These results in vitro imitated the results in vivo, and indicated at least that in the immediate stage of activation of mast cells, Lyn is important to the activation of signaling of FcRs.

B-3 (Normal Function of FcγRIII to Cytokine Production in BMMCs of Double Deficient Mice)

Figure 4:
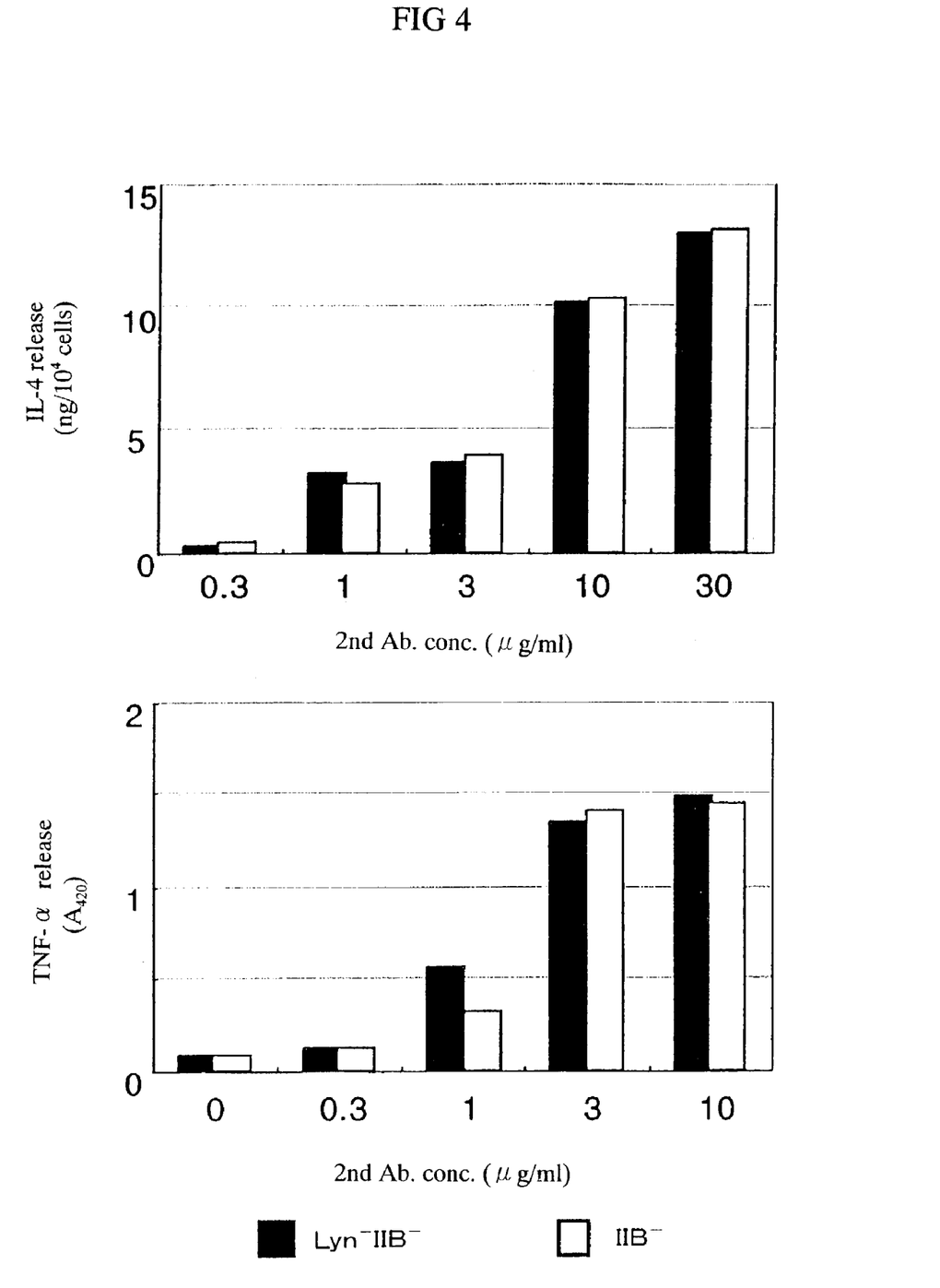
FIG. 4 is a view showing the results from determination of cytokine discharge from bone marrow-derived mast cell of the double deficient mice (Lyn⁻IIB⁻) of the present invention and control mice (IIB⁻) which is induced by cross linkage of FcγRIII.

It has been revealed cytokines are newly produced by stimulation through FcR in mast cells (Nature 339, 64-67, 1989; J. Exp. Med. 170, 245-257, 1989; Nature 346, 274-276, 1990; Int. Arch. Allergy Immunol. 107, 158-159, 1995). The cytokines TNF-α and IL-4 that are well studied with regard to the activation of mast cells, are actually released in two hours, three hours or several hours after stimulation through FcR. It has been indicated that the cytokine release of mast cell is important to the onset of tissue destruction involving mast cell (Blood 94, 3855-3863, 1999; Immunology 77, 422-427, 1992; Science 258, 1957-1959, 1992) and allergy (Allergy 50, 851-862, 1995). Based on these facts, the amount of production of TNF-α and IL-4 from BMMCs induced by stimulation through FcR was examined. The BMMCs were stimulated for a few hours according to the method described in Example A-4 to crosslink FcγR, under a condition wherein anti-FcγRII/III antibody (2.4G2) and various concentrations of secondary antibodies exist. The results are shown in FIG. 4. The results, contrary to the results obtained by degranulation and biochemical assay shown in FIGS. 2 and 3, did not show effect in the induction of TNF-α and IL-4 in double deficient mouse-derived BMMCs. These results indicate that the cytokine gene is activated regardless of Lyn activity in the downstream of FcγRIII signaling, and suggests the existence of a signaling mechanism sufficient for the induction of cytokine production in the mast cell.

B-4 (Normal Function of FcγRIII to Reverse Cutaneous Passive Arthus Reaction in Lyn Deficient Mice)

Figure 5:
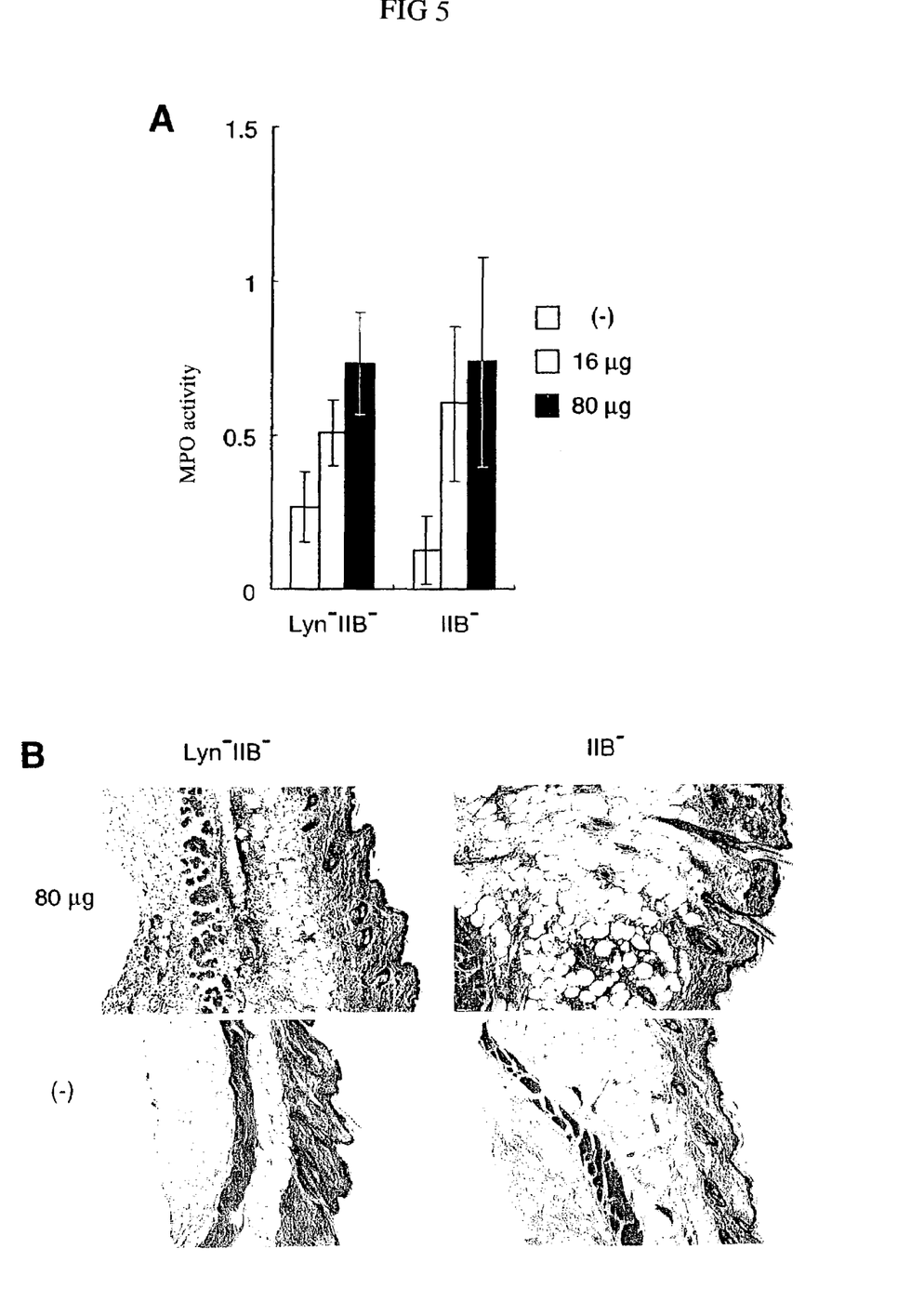
FIG. 5 is a view showing the MPO activity of the inflammation site (A) and histological change (B) of the reverse cutaneous passive Arthus reaction of the double deficient mice (Lyn⁻IIB⁻) of the present invention and control mice (IIB⁻) induced by IgG-immunocomplex.

Based on the result mentioned above wherein the production of cytokine does not depend on Lyn in vitro, the reverse cutaneous passive Arthus reaction, where cytokine is thought to be important to the expression thereof, was examined. This reverse cutaneous passive Arthus reaction is an inflammatory model caused by immunocomplex in vivo, and is revealed that it depends on the FcγRIII function on the mast cell (Science 265, 1095-1098, 1994; Immunity 5, 387-390; J. Clin. Invest. 99, 915-925, 1997; J. Clin. Invest. 99, 901-914, 1997; Immunity 5, 181-188, 1996). The MPO (myeloperoxidase) activity was measured according to the method as described in Example A-7 mentioned above, and examination by histology was also conducted. The results are shown in FIG. 5. In FIG. 5(A), the infiltration rate of neutrophil is presented by the MPO activity (mean value±standard deviation of five mice wherein 1 unit is equivalent to MPO activity in 0.25 μl) of the inflammmatory site eight hours after administration of antigen. In FIG. 5(B), the histological change stained by hematoxylin eosin eight hours after induction of inflammation is shown together with a control sample (−) in which physiological saline had been intracutaneously administered (all photographs show observation at 40 magnifications). It was revealed from these results that the induction and histological view of MPO activity are in the same level for both the double deficient mice and control mice. It is clear that the number of mast cells in the skin is normal for the double deficient mice. It was revealed that the signaling activity that does not depend on Lyn of FcγRIII is sufficient to develop reverse cutaneous passive Arthus reaction, and that Lyn is not indispensable for the start of reaction at the later period of mast cells.

INDUSTRIAL APPLICABILITY

The non-human model animal for type III allergy inflammation in the present invention that does not develop anaphylaxis, a type I allergy, and can specifically induce Arthus reaction, a type III allergy, for example, a double knockout mouse wherein the genetic function of Lyn and FcγIIB are deficient on its chromosome, is not affected by type I allergy, and is useful as an experimental model animal capable of evaluating type III allergy inflammation independently. Further, screening for an allergy reaction accelerating or inhibitory substance specific to type III allergy reaction through FcγRIII can be done by using said experimental model animal. There is a possibility that the inhibitory substance obtained by screening can be used as a remedy for diseases caused by type III allergy reaction.

The invention claimed is:

1. A mouse model for type III allergy inflammation wherein the mouse does not develop anaphylaxis, a type I allergy, and specifically induces Arthus reaction, a type III allergy, wherein the genome of said mouse model comprises a homozygous disruption of Lyn and FcγRIIB genes, and said model mouse produces neither FcγRIIB nor Lyn proteins.

* * * * *